United States Patent [19]

Shimizu et al.

[11] 4,016,216
[45] * Apr. 5, 1977

[54] STABILIZING 2,3-DICHLORO-1,3-BUTADIENE WITH CERTAIN N-NITROSOANILINE COMPOUNDS

[75] Inventors: Akihiko Shimizu; Takao Hayashi, both of Shin-nanyo, Japan

[73] Assignee: Toyo Soda Manufacturing Co., Ltd., Japan

[ * ] Notice: The portion of the term of this patent subsequent to Mar. 22, 1994, has been disclaimed.

[22] Filed: July 31, 1975

[21] Appl. No.: 600,565

Related U.S. Application Data

[63] Continuation-in-part of Ser. No. 444,014, Feb. 20, 1974, abandoned.

[30] Foreign Application Priority Data

Feb. 20, 1973  Japan .............................. 48-19783

[52] U.S. Cl. ....................... 260/652.5 P; 252/403; 260/652.5 R
[51] Int. Cl.² ......................................... C07C 17/42
[58] Field of Search ............... 260/652 P, 652.5 R, 260/652.5 P; 252/182, 403

[56] References Cited

UNITED STATES PATENTS

| | | | |
|---|---|---|---|
| 3,015,677 | 1/1962 | Vogt et al. ................... | 260/652.5 P |
| 3,082,262 | 3/1963 | Scott ....................... | 260/652.5 P |
| 3,275,531 | 9/1966 | Sennewald et al. .......... | 260/652.5 P |
| 3,634,526 | 1/1972 | Benjamins ................... | 260/652.5 P |
| 3,769,228 | 10/1973 | Michaelson .................... | 252/182 X |

FOREIGN PATENTS OR APPLICATIONS

| | | | |
|---|---|---|---|
| 1,008,819 | 11/1965 | United Kingdom ......... | 260/652.5 P |
| 971,969 | 10/1964 | United Kingdom ......... | 260/652.5 P |

*Primary Examiner*—Daniel E. Wyman
*Assistant Examiner*—Thomas A. Waltz
*Attorney, Agent, or Firm*—Oblon, Fisher, Spivak, McClelland & Maier

[57] ABSTRACT

Polymerization of 2,3-dichloro-1,3-butadiene is inhibited by adding an aniline compound having an N-nitroso group which can be easily removed with an alkaline aqueous solution to the 2,3-dichloro-1,3-butadiene.

7 Claims, No Drawings

STABILIZING 2,3-DICHLORO-1,3-BUTADIENE WITH CERTAIN N-NITROSOANILINE COMPOUNDS

CROSS-REFERENCE TO RELATED APPLICATIONS

The application is a continuation-in-part of U.S. patent application Ser. No. 444,014, filed Feb. 20th, 1974, now abandoned.

BACKGROUND OF THE INVENTION

1. Field of the Invention

This invention relates to a process for stabilizing 2,3-dichloro-1,3-butadiene against polymer formation.

2. Description of the Prior Art 2,3-Dichloro-1,3-butadiene is a well known monomer which is easily polymerizable, and polymers thereof are disadvantageously formed in the manufacture, distillation, or storage of the monomer.

These polymers are undesirable because they are usually insoluble and adhere to the apparatus used for the manufacture or treatment of the monomer, resulting in the clogging of conduits and other parts of the apparatus. This clogging causes difficulty in the operation of the apparatus, which is a serious industrial disadvantage.

Also, the formation of the polymer in the storage of the monomer causes an undesirable decrease in the purity of the 2,3-dichloro-1,3-butadiene monomer.

2,3-Dichloro-1,3-butadiene is generally not used alone but is generally used to form copolymers together with other monomers such as 2-chloro-1,3-butadiene. Before the 2,3-dichloro-1,3-butadiene monomer is used, any precipitated polymers of 2,3-dichloro-1,3-butadiene formed in storage have to be removed. The polymers have been removed by redistillation. However, the redistillation of the monomer before use is a difficult operation because of the ease with which the monomers are polymerized. When a large amount of the monomer is required, the redistillation becomes practically impossible.

If the monomer containing these polymers is used without separation of the polymers, the undesirable polymers adhere to the polymerization apparatus to cause an adverse effect on the property of the resulting product. Accordingly, the inhibition of the formation of polymers from 2,3-dichloro-1,3-butadiene monomers remains in need of a solution. One attempted solution for inhibiting the polymerization of 2,3-dichloro-1,3-butadiene requires the refrigeration of the monomer with the addition of t-butyl catechol. Another attempted solution includes the addition of a piperidine derivative to the monomer. However, satisfactory results have not been obtained by these conventional methods. Accordingly, a need therefore exists for a process to stabilize 2,3-dichloro-1,3-butadiene from polymerizing.

SUMMARY OF THE INVENTION

Accordingly, one object of this invention is to stabilize 2,3-dichloro-1,3-butadiene in an industrially advantageous process.

Another object of this invention is to provide a stabilized 2,3-dichloro-1,3-butadiene composition.

Yet another object is to provide a stabilized 2,3-dichloro-1,3-butadiene composition from which the stabilizer is readily removed.

Briefly, these and other objects of the invention, as will hereinafter become apparent, are achieved by adding an aniline derivative having an N-nitroso group which can be easily removed by washing with an aqueous alkaline solution to 2,3-dichloro-1,3-butadiene.

DETAILED DESCRIPTION OF THE PREFERRED EMBODIMENTS

The aniline derivatives having an N-nitroso group used as a polymerization inhibitor include the compounds having the formula:

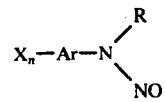

wherein R represents a $C_{1-8}$ alkyl group, or a carboxymethyl group; and when R is a $C_{1-8}$ alkyl group, X is hydroxy and when R is a carboxymethyl group, X is a halogen or hydroxyl group and $n$ is 1 or 2.

Suitable anilines having an N-nitroso group include N-nitroso-N-phenylglycine, N-nitroso-N-p-chlorophenylglycine, N-nitroso-N-p-hydroxyglycine, N-nitroso-N-methyl-p-hydroxyaniline, N-nitroso-N-butyl-m,p-dihydroxyaniline and the like. The polymerization inhibitor may be used alone or together with t-butyl catechol.

The amount of polymerization inhibitor added depends upon the temperature, length of time the monomer system containing 2,3-dichloro-1,3-butadiene is to be stored, and operation time and conditions of the monomer system. However, the amount is usually 0.001–0.5 part by weight and preferably 0.01–0.1 part by weight per 100 parts by weight of the 2,3-dichloro-1,3-butadiene monomers. The inhibitor may be added to the monomers during preparation of the monomer, distillation or storage.

The use of the stabilized composition is not limited. For example, in storage, the polymerization inhibitor can be dissolved in 2,3-dichloro-1,3-butadiene or a methanol solution thereof. In a distillation, 0.01–0.1 part by weight of the polymerization inhibitor can be added to 100 parts by weight of 2,3-dichloro-1,3-butadiene whereby high purity, 2,3-dichloro-1,3-butadiene is obtained. During the distillation, no precipitation of the polymer is observed.

In the polymerization of 2,3-dichlorobutadiene, it is not suitable to use 2,3-dichlorobutadiene containing the inhibitor. It is necessary to remove the inhibitor before use. In order to remove the conventional nitroso compounds such as N-nitroso-diphenylamine, the monomer containing the inhibitor is usually distilled. However, the distillation method is disadvantageous economically and is a time-consuming operation. The inhibitors of the invention are soluble in an aqueous alkaline solution. Accordingly, the inhibitors can be easily removed by washing 2,3-dichlorobutadiene monomer containing the inhibitor with an aqueous alkaline solution, such as sodium hydroxide, sodium carbonate, potassium hydroxide, or the like.

In the process, 2,3-dichlorobutadiene containing the inhibitor is mixed with stirring with an aqueous alkaline solution for a certain time. Stirring is then stopped and the mixture is allowed to stand so that it separates into an upper phase of 2,3-dichlorobutadiene and a lower phase of an aqueous alkaline solution containing the inhibitor. The aqueous alkaline solutions used in the invention can be aqueous solutions of alkali metal hydroxide such as sodium hydroxide and potassium hydroxide.

The concentration of the alkali metal hydroxide is usually in a range of 0.005 to 20 wt. %, preferably 1 to 10 wt. %. The ratio of the aqueous alkali solution to 2,3-dichlorobutadiene containing the inhibitor is in a range of 0.1 to 10, preferably 0.5 to 3 by volume. The time for stirring is usually 5 to 60 minutes. The number of times the monomer is washed is not limited and is usually from 1 to 5 times. Preferably, the monomer is washed two or more times in order to substantially remove the inhibitor. This is quite advantageous in an industrial operation. The polymerization inhibitor can also be removed by distillation.

The 2,3-dichloro-1,3-butadiene may be in the form of a pure liquid, an emulsion or a solvent solution. Various well known solvents may be used. However, the solvents are preferably alcohols such as methanol, ethanol or the like. The solvents may also be aromatic solvents such as benzene, toluene, or the like. The solvents also include mixtures of these compounds.

Having generally described the invention, a more complete understanding can be obtained by reference to certain specific examples, which are included for purposes of illustration only and are not intended to be limiting unless otherwise specified.

REFERENCE EXAMPLE 1

0.2 Part of t-butyl catechol was added to 100 parts of a 40% methanol solution of 2,3-dichloro-1,3-butadiene monomer in a tank which was purged with nitrogen and sealed, and kept in a vessel maintained at 40° C. After 3 days, a lot of polymer precipitation was observed.

EXAMPLES 1-2

Each of the polymerization inhibitors shown in Table 1 was added to the 2,3-dichloro-1,3-butadiene monomer and kept as set forth in Reference Example 1.

The results are shown in Table 1. A remarkable stabilizing and inhibiting effect on polymerization was observed for the monomers containing the stabilizers of the present invention.

TABLE 1

| | Effect of stabilization of 2,3-dichloro-1,3-butadiene[1] | | | |
|---|---|---|---|---|
| Ex. | Polymerization inhibitor | Amount (phm)[3] | TBC[2] (phm) | Test Result |
| 1 | N-nitroso-N-phenylglycine | 0.01 | 0.1 | No polymer precipitation was found after 30 days |
| 2 | N-nitroso-N-methyl-p-hydroxyaniline | 0.01 | 0.1 | " |

Note:
[1]A methanol solution containing 40 wt. % of 2,3-dichloro-1,3-butadiene was used for the test.
[2]TBC indicates t-butylcatechol.
[3]phm: parts per hundred monomer.

REFERENCE EXAMPLE 2

100 Parts of a 40% methanol solution of 2,3-dichlorobutadiene containing 0.1 part of N-nitroso-diphenylamine was washed with 200 parts of 10% aqueous solution of sodium hydroxide for 1 hour. 20 Parts of the monomer and 80 parts of chloroprene were emulsified with 100 parts of water and 3 parts of potassium rosin acid salt. 0.5 Part of potassium persulfate was added to the emulsion and the polymerization was conducted at 40° C for 4 hours. No polymer was obtained.

EXAMPLE 3

The process of Reference Example 2 was repeated except that 0.1 part of N-nitroso-N-phenylglycine was used instead of N-nitroso-diphenylamine. After 3 hours, 70% conversion for the polymerization reaction was found because of the removal of the initiator by the alkali washing.

EXAMPLE 4

In the process of Example 3, 100 parts of a methanol solution of 2,3-dichlorobutadiene containing 0.1 part of N-nitroso-N-methyl-p-hydroxyaniline and 0.1 part of butyl catechol instead of N-nitroso-N-phenylglycine was washed two times with 70 parts of a 3% aqueous solution of potassium hydroxide for 30 minutes. In accordance with the process of Reference Example 2, the resulting monomer was polymerized. After 3 hours, 70% conversion for the polymerization reaction was found.

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. A composition comprising 2,3-dichloro-1,3-butadiene stabilized against polymerization with an effective amount of an aniline compound having an N-nitroso group and having the formula:

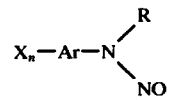

wherein Ar is phenyl; R represents a $C_{1-8}$ alkyl group or a carboxymethyl group and when R is a $C_{1-8}$ alkyl group, X is hydroxy and when R is carboxymethyl, X is a halogen or hydroxyl group and $n$ is 1 or 2 to, whereby said N-nitrosoaniline is easily removed from said monomer by washing the same with an aqueous alkaline solution.

2. The composition of claim 1, wherein 0.01 to 0.1 part by weight of said aniline compound is added to 100 parts by weight of 1,3-dichloro-1,3-butadiene.

3. The composition of claim 1, wherein said aniline compound having an N-nitroso group is added to 2,3-dichloro-1,3-butadiene or a solvent solution of said 2,3-dichloro-1,3-butadiene dissolved therein in the preparation of the 2,3-dichloro-1,3-butadiene monomer.

4. The composition of claim 1, wherein said aniline compound having an N-nitroso group is added to the 2,3-dichloro-1,3-butadiene or a solvent solution thereof in the storage of the 2,3-dichloro-1,3-butadiene.

5. The composition of claim 1, wherein said aniline compound having an N-nitroso group is added to 2,3-dichloro-1,3-butadiene and thereafter distilled.

6. The composition of claim 1, wherein said aniline compound having an N-nitroso group is added to a mixture of 2,3-dichloro-1,3-butadiene and 2-chloro-1,3-butadiene.

7. The composition of claim 1, wherein the aniline compound having an N-nitroso group is selected from the group consisting of N-nitroso-N-phenylglycine, N-nitroso-N-p-chlorophenylglycine, N-nitroso-N-p-hydroxyglycine, N-nitroso-N-methyl-p-hydroxyaniline and N-nitroso-N-butyl-m,p.-dihydroxyaniline.

* * * * *